United States Patent [19]
Critchley et al.

[11] Patent Number: 5,415,855
[45] Date of Patent: May 16, 1995

[54] COSMETIC COMPOSITION

[75] Inventors: Peter Critchley, Bedford; Susan E. Kirsch, St. Albans, both of United Kingdom; Anthony V. Rawlings, Wyckoff; Ian R. Scott, Allendale, both of N.J.

[73] Assignee: Elizabeth Arden Co., Division of Conopco, Inc., New York, N.Y.

[21] Appl. No.: 78,322

[22] PCT Filed: Oct. 21, 1991

[86] PCT No.: PCT/GB91/01838

§ 371 Date: Jun. 22, 1993

§ 102(e) Date: Jun. 22, 1993

[87] PCT Pub. No.: WO92/06674

PCT Pub. Date: Apr. 30, 1992

[30] Foreign Application Priority Data

Oct. 22, 1990 [GB] United Kingdom ............... 9022921

[51] Int. Cl.⁶ .................. A61K 7/04; A61K 7/075; A61K 7/40; A61K 7/48; C07C 305/04; C07F 9/141; C07H 11/04

[52] U.S. Cl. .................. 424/61; 424/70.1; 424/401; 424/DIG. 1; 424/DIG. 5; 252/DIG. 5; 252/DIG. 13; 514/23; 514/25; 514/103; 514/114; 514/475; 514/517; 514/552; 514/781; 514/844; 514/846; 514/883; 514/887; 514/936; 514/937; 514/938; 536/171; 536/172; 536/175; 549/15; 549/548; 554/40; 554/41; 554/44; 554/46; 554/49; 554/63; 554/66; 558/22; 558/25; 558/159

[58] Field of Search .......... 424/401, 70, 61, DIG. 1, 424/DIG. 5; 252/DIG. 13, DIG. 5, 23; 514/25, 781, 844, 846, 883, 887, 936, 937, 938, 103, 114, 517, 475, 517, 552; 558/22, 25, 28, 30, 159, 172, 174; 554/40, 41, 44, 46, 49, 63, 66; 549/15, 548; 536/171, 172, 175

[56] References Cited

U.S. PATENT DOCUMENTS 4,950,688  8/1990  Bowser et al. ................. 514/847
5,198,210  3/1993  Critchley et al. .............. 424/401
5,202,357  4/1993  Bowser et al. ................. 514/847
5,206,020  4/1993  Critchley et al. .............. 424/401

FOREIGN PATENT DOCUMENTS 0097059  12/1983  European Pat. Off. .
0227994   7/1987  European Pat. Off. .
0282816   9/1988  European Pat. Off. .
0455429  11/1991  European Pat. Off. .
2178312   2/1987  United Kingdom .
2213723   6/1988  United Kingdom .

OTHER PUBLICATIONS

JP 125699 (1988) Abstract.
JP 192703 (1988) Abstract.
PCT International Search Report.
Abstract of Japanese Patent Specification 63/192703.
Chemical Abstracts 92:41295t.
Chemical Abstracts 90:167984u.
Abstract of Japanese Patent Specification 89/299265.

*Primary Examiner*—Jyothsna Venkat
*Attorney, Agent, or Firm*—Rimma Mitelman

[57] ABSTRACT

Modified ceramides are defined, together with their synthesis and compositions comprising them for topical application to human skin, hair and nails. The modified pseudoceramides have a structure:

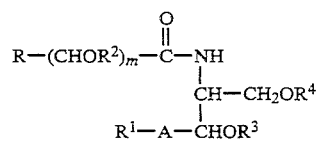

and an approximate summary is that R and $R^1$ are aliphatic hydrocarbon, A is $CH_2$, $CHOR^2$, $CH=CH$ or CHOY, and at least one of $R^2$, $R^3$ and $R^4$ is sulphate, phosphate or similar. The presence of phosphate or sulphate facilitates skin absorption, after which the phosphate or sulphate is removed by enzymes present in vivo.

7 Claims, No Drawings

COSMETIC COMPOSITION

FIELD OF THE INVENTION

The invention relates to modified ceramides, their synthesis and use in compositions for topical application to human skin, hair or nails.

BACKGROUND TO THE INVENTION AND PRIOR ART

It is generally understood that ceramides present within the intercellular lipid lamellae of the stratum corneum play an important role in the production and maintenance of the water permeability barrier of the skin. Ceramides, or substances closely related to them, have been disclosed as components of skin care compositions. In particular, Kao Corporation in GB 2 178 312 and GB 2 213 723 disclose the use of natural ceramides extracted from skin in topical products. Also, Unilever in EP 97059 disclose -linoleoyl ceramides and emphasize their role in the water barrier function of the skin.

It is believed that one of the causes of dry skin and ageing skin is a reduction in the amount of lipid contained within these intercellular lipid lamellae. It is therefore desirable to be able successfully to replace these depleted lipids via the topical route.

One of the problems associated with the topical application of skin and hair care products containing ceramides or their synthetic analogues, is devising a suitable method for delivering them effectively to the lipid lamellae, without causing permanent disruption of the stratum corneum. It is accordingly apparent that permanently disrupted stratum corneum is unable to retain molecules of this sort, as they are simply washed out again when the stratum corneum (skin) is contacted with water.

This problem has not successfully been solved to date.

Kao Corporation have reported in GB 2 178 312, EP 227 994 and EP 282 816, that co-surfactants such as glyceryl ethers assist synthetic ceramide, to penetrate into the stratum corneum. However, these co-surfactants tend to disrupt the stratum corneum, so that when penetration occurs allowing the synthetic ceramide access to the lipid lamellae, there is nothing to prevent them being washed out again on contact with water.

Certain phosphorylated and sulphated derivatives of ceramides have been prepared in the course of scientific investigation of natural metabolism or to make liposomes for drug delivery.

Thus Karpyshev, Bushnev et al Bioorg Khim 5(2) 238 (1979) and 5(9) 1381 (1979) describe preparation of phosphorylated derivatives of ceramides by routes which entail the use of protective groups which are eventually removed.

Japanese published application JP-A-89/299265 discloses the preparation of ceramide sulphates to be used for liposome production.

SUMMARY OF THE INVENTION

We have solved the problem of effective delivery of ceramides using modified naturally-occurring ceramides, that is ceramides derived from animal tissues, such as skin and brain or those derived from certain plant tissues, which have been modified by phosphorylation and/or sulphation.

Accordingly, when these modified ceramides are applied topically to the skin, together with a suitable cosmetically acceptable vehicle, they will readily penetrate the stratum corneum without permanently disrupting it, and after demodification with phosphatases or sulphatases which occur naturally in skin and which will cleave off the phosphate or sulphate groups respectively, the unmodified ceramide structures will remain locked in the desired location within the stratum corneum. Since the phosphate and/or sulphate groups, which facilitate delivery, have been removed once the ceramide is in position, it is then not possible subsequently to wash out the ceramide from the skin, so ensuring that it is available to effect repair in situ of lipid lamellae which have become damaged under dry skin conditions.

To summarise: we have modified certain naturally-occurring ceramides by phosphorylation or sulphation to assist their penetration into the lipid lamellae of the stratum corneum. Once located within the lipid lamellae, naturally-occurring phosphatases and sulphatases will cleave off the phosphate or sulphate groups respectively, to leave the ceramides lodged firmly within the stratum corenum.

DEFINITION OF THE INVENTION

Accordingly, one aspect of this invention provides a composition for topical application to human skin, hair or nails which comprises:

i. an effective amount of at least one modified ceramide having the structure (1) below; and ii. a cosmetically acceptable vehicle for the modified ceramide.

The modified ceramide structure (1) is:

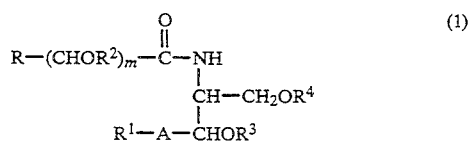

where

A represents —$CH_2$ or —$CHOR^2$ or —CH=CH— or —CHOY—

R represents a linear or branched, saturated or unsaturated, hydroxylated or non-hydroxylated, phosphorylated or non-phosphorylated, sulphated or non-sulphated aliphatic hydrocarbon group having from 8 to 49 carbon atoms or the group Y—O—(-$C_aH_b$)—

$R^1$ represents a linear or branched, saturated or unsaturated, hydroxylated or non-hydroxylated, phosphorylated or non-phosphorylated, sulphated or non-sulphated, aliphatic hydrocarbon having from 8 to 28 carbon atoms;

$R^2$ & $R^3$ individually represent H or a phosphite residue ($P_i$), or a sulphite residue ($SO_3^\ominus$), $P_i$ represents

$R^4$ represents H, a, phosphite residue ($P_i$), a sulphite residue ($SO_3^-$), a sugar residue or the groups

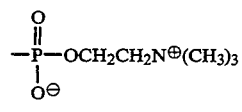 (2)

or

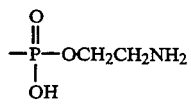 (3)

or

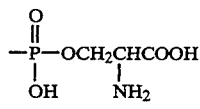 (4)

or

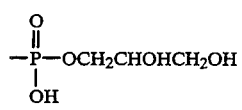 (5)

or

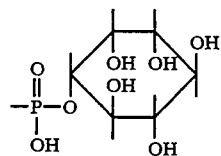 (6)

a is an integer of from 7 to 49
b is an integer of from 10 to 98
m is 0 or 1
Y represents H or a residue of a $C_{14}$ to $C_{22}$ fatty acid having the structure (7)

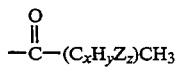 (7)

where
Z is —OH or an epoxy oxygen
x is an integer of from 12 to 20
y is an integer of from 20 to 40
z is 0, or an integer of from 1 to 4;
provided that at least one out of $R^2$ $R^3$ & $R^4$ is either a phosphate residue or a sulphate residue.

FURTHER DISCLOSURE OF THE INVENTION

The Modified Ceramide

With reference to structure (1), the group R preferably represents an aliphatic hydrocarbon group having from 12 to 30 carbon atoms, while the group $R^1$ preferably represents an aliphatic hydrocarbon group having from 12 to 22 carbon atoms.

Also, with reference to structure (1), the value of "a" is preferably an integer of from 24 to 30 and the value of "b" is preferably an integer of from 44 to 60.

Also, with reference to structure (1), the group Y represents a straight chain saturated $C_{16-18}$, fatty acid residue or a straight chain all cis n-6,9 di-unsaturated $C_{16-18}$ fatty acid residue.

Specific examples of these modified ceramides are those having the structures (8)–(25).

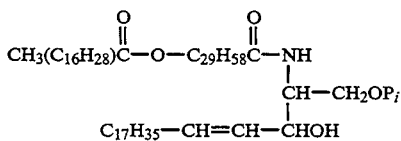 (8)

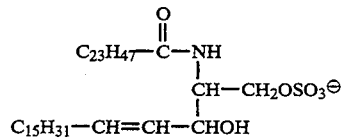 (9)

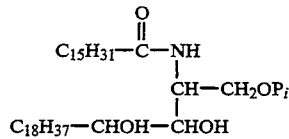 (10)

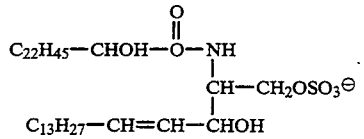 (11)

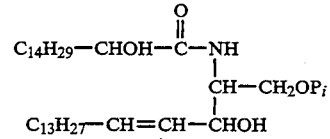 (12)

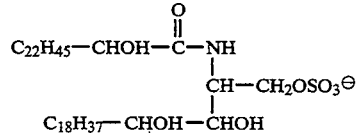 (13)

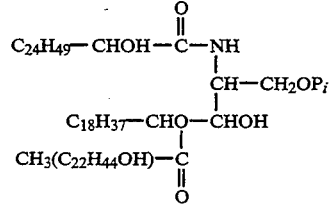 (14)

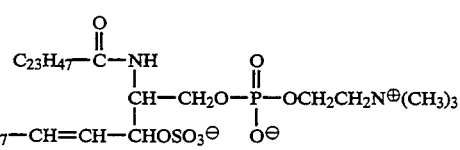 (15)

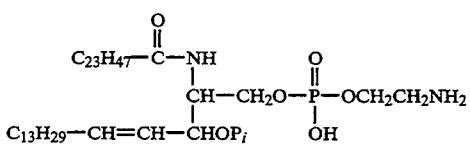 (16)

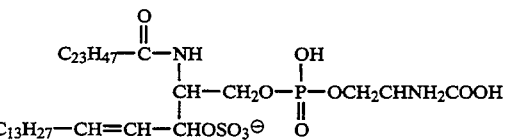 (17)

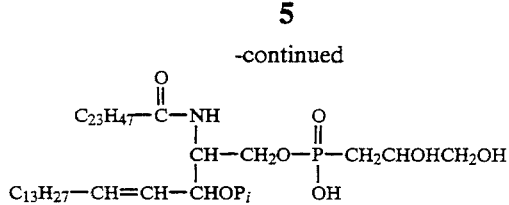
(18)

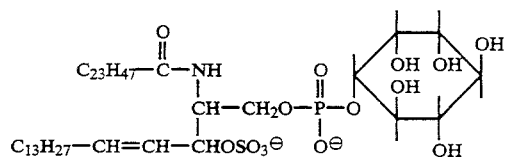
(19)

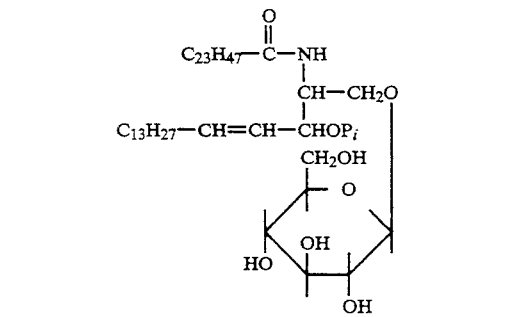
(20)

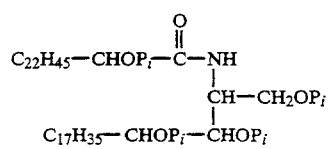
(21)

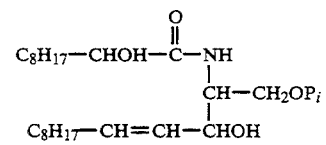
(22)

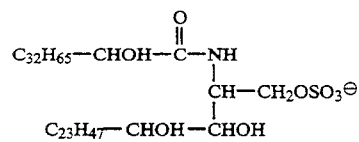
(23)

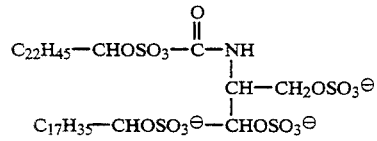
(24)

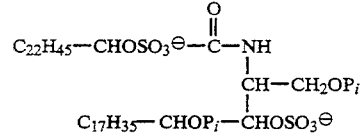
(25)

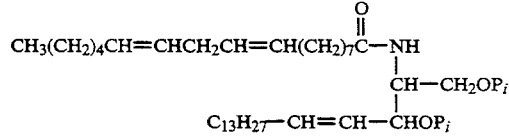
(26)

SYNTHESIS OF THE MODIFIED CERAMIDES

The modified ceramides according to the invention can be synthesised using a conventional method involving phosphorylation and/or sulphation.

Examples of phosphorylation comprise the treatment of a naturally-occurring ceramide, or mixtures thereof, with one of the following:

(i) phosphorus pentoxide ($P_2O_5$), (ii) polyphosphonic acid, (iii) phosphorus oxychloride, ($POCl_3$) followed by hydrolysis, or (iv) phosphorus trichloride ($PCl_3$) followed by:
 (a) oxidation using, for example, chlorine, and then
 (b) hydrolysis.

Examples of sulphation comprise the treatment of a naturally-occurring ceramide, or mixture thereof with one of the following:

(i) chlorosulphonic acid, (ii) thionylchloride, ($SOCl_2$), or (iii) fuming sulphuric acid.

The naturally-occurring ceramide can either be synthesised or isolated from a suitable animal or plant source.

Particulary preferred sources of naturally-occurring ceramides are pig skin or neutral tissue. A preferred technique for isolation of ceramides from pig skin involves the use of "pig bristle", this being the pulp or slurry obtained from the pig carcass following mechanical flailing or scrubbing of the skin to remove hair or bristle prior to butchering to provide the useful parts of the animal for consumption. In accordance with this technique, the so-called pig bristle, as a pulp or slurry, is de-watered as far as it is possible, using filtration or centrifugation. The de-watered pig bristle is then preferably dried, for example with hot air, and then extracted with an organic solvent such as isopropyl alcohol and methyl alcohol, optionally together with chloroform.

A mixture of ceramides can then be isolated from this solvent extract and treatment with one of the above mentioned methods, (preferably, with phosphorus pentoxide and/or chlorosulphonic acid) can then be employed in accordance with the conventional technology to achieve phosphorylation and/or sulphation, respectively, of the purified pig skin ceramides.

A similar procedure involving phosphorylation and/or sulphation can be employed to modify purified naturally-occurring ceramides, to their respective phosphorylated and/or sulphated forms.

The material which is subjected to sulphation or phosphorylation, whether natural or synthetic in origin, will preferably be of structure:

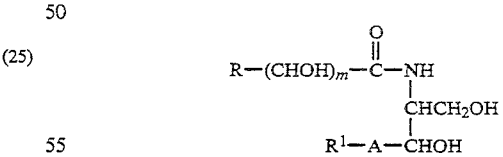

in which A is $—CH_2—$ or $—CHOH—$ or $—CH=CH—$ or $—CHOY—$ while R, $R^1$ and m are as defined above.

Phosphorylation or, as the case may be, sulphation will preferably be carried out under conditions where any hydroxyl group present in the starting material can react. This then leads to (at least some) formation of product compounds in which neither $R^2$ nor $R^3$ nor $R^4$ is H. It can also convert any other hydroxyl groups present as substituents on R or $R^1$ into phosphate or sulphate groups. There may be sulphation or phosphorylation of all free hydroxyl groups in the starting material. Such uncontrolled sulphation or phosphorylation is economical and is acceptable because it is intended that the sulphate or phosphate groups will be removed in vivo by naturally occurring enzymes.

DEFINITION OF COMPOUNDS OF THE INVENTION

In another aspect, therefore, the invention provides modified ceramides having the structure (1) as defined above except that none of $R^2$ nor $R^3$ nor $R^4$ is H.

FURTHER DISCLOSURE OF THE COMPOSITION

The composition according to the invention comprises in its simplest form a modified ceramide of structure (1) above and a vehicle therefor to enable the modified ceramide to be dispersed onto the skin and distributed thereon.

The amount of the modified ceramide, or a mixture thereof, present in the composition according to the invention is from 0.00001 to 50%, preferably from 0.001 to 20% and most preferably from 0.1 to 10% by weight.

The Cosmetically Acceptable Vehicle

The composition according to the invention also comprises a cosmetically acceptable vehicle to act as a dilutant, dispersant or carrier for the modified ceramide in the composition, so as to facilitate its distribution when the composition is applied to the skin and/or hair.

Vehicles other than water can include liquid or solid emollients, solvents, humectants, thickeners and powders.

Examples of each of these types of vehicle, which can be used singly or as mixtures of one or more vehicles, are as follows:

Emollients, such as stearyl alcohol, glyceryl monoricinoleate, glyceryl monostearate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, evening primrose oil, soybean oil, sunflower seed oil, avocado oil, olive oil, sesame seed oil, coconut oil, arachis oil, castor oil, acetylated lanolin alcohols, petroleum jelly, mineral oil, butyl myristate, isostearic acid, palmitatic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the emulsion, and can, in the absence of other cosmetic adjuncts, form the balance of the composition.

OPTIONAL SKIN BENEFIT MATERIALS AND COSMETIC ADJUNCTS

A particularly convenient form of the composition according to the invention is an emulsion, in which case an oil or oily material will normally be present, together with an emulsifier to provide either a water-in-oil emulsion or an oil-in-water emulsion, depending largely on the average hydrophilic-lyophilic balance (HLB) of the emulsifier employed.

Oil or oily material

The composition according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and non-volatile, such as polydimethyl siloxanes.

The oil or oily material, when present for the purposes for forming an emulsion, will normally form up to 90%, preferably from 10 to 80% by volume of the composition.

Emulsifier

The composition according to the invention can also optionally comprise one or more emulsifiers the choice of which will normally determine whether a water-in-oil or and oil-in-water emulsion is formed.

When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of >6.

Examples of suitable emulsifiers are set below in Table 1 in which the chemical name of the emulsifiers is given together with an example of a trade name as commercially available, and the average HLB value.

TABLE 1

| Chemical Name of Emulsifier | Trade Name | HLB Value |
|---|---|---|
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Arlacel 60 | 4.7 |
| Poloxyethylene (2) stearyl ether | Brij 72 | 4.9 |
| Poloxyethylene sorbitol beeswax derivative | G-1702 | 5 |
| PEG 200 dilaurate | Emerest 2622 | 6.3 |
| Sorbitan monopalmitate | Arlacel 40 | 6.7 |
| Polyoxyethylene (3.5) nonyl phenol | Emulgen 903 | 7.8 |
| PEG 200 monostearate | Tegester PEG 200 MS | 8.5 |
| Sorbitan monolaurate | Arlacel 200 | 8.6 |
| PEG 400 dioleate | Tegester PEG 400-DO | 8.8 |
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl | Brij 30 | 9.7 |

TABLE 1-continued

| Chemical Name of Emulsifier | Trade Name | HLB Value |
|---|---|---|
| ether | | |
| Polyoxyethylene (5) sorbitan monooleate | Tween 81 | 10.0 |
| PEG 300 monooleate | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene (8) monostearate | Myrj 45 | 11.1 |
| PEG 400 monooleate | Emerest 2646 | 11.7 |
| PEG 400 monostearate | Tegester PEG 400 | 11.9 |
| Polyoxyethylene 10 monooleate | Ethofat 0/20 | 12.2 |
| Polyoxyethylene (10) stearyl ether | Brij 76 | 12.4 |
| Polyoxyethylene (10) cetyl ether | Brij 56 | 12.9 |
| Polyoxyethylene (9.3) octyl phenol | Triton X-100 | 13.0 |
| Polyoxyethylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxyethylene sorbitol lanolin derivative | G-1441 | 14.0 |
| Polyoxyethylene (12) lauryl ether | Ethosperse LA-12 | 14.4 |
| PEG 1500 dioleate | Pegosperse 1500 | 14.6 |
| Polyoxyethylene (14) laurate | Arosurf HFL-714 | 14.8 |
| Polyoxyethylene (20) sorbitan monostearate | Tween | 14.9 |
| Polyoxyethylene 20 sorbitan monooleate | Tween 80 | 15.0 |
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene monostearate | G-2162 | 16.0 |
| Polyoxyethylene (20) sorbitol monolaurate | Tween 20 | 16.7 |
| Polyoxyethylene (23) lauryl ether | Brij 35 | 16.9 |
| Polyoxyethylene (50) monostearate | Myrj 53 | 17.9 |
| PEG 4000 monostearate | Pegosperse 4000 MS | 18.7 |

The foregoing list of emulsifiers is not intended to be limiting and merely exemplifies selected emulsifiers which are suitable for use in accordance with the invention.

It is to be understood that two or more emulsifiers can be employed if desired.

The amount of emulsifier or mixtures thereof, to be incorporated in the composition of the invention, when appropriate is from 1 to 50%, preferably from 2 to 20% and most preferably from 2 to 10% by weight of the composition.

Water

The composition of the invention can also comprise water, usually up to 98%, preferably from 5 to 80% by volume.

Silicone Surfactant

The composition of the invention can also optionally comprise a high molecular weight silicone surfactant which can also act as an emulsifier, in place of or in addition to the optional emulsifier(s) already mentioned.

The silicone surfactant is a high molecular weight polymer of dimethyl polysiloxane with polyoxyethylene and/or polyoxypropylene side chains having a molecular weight of from 10,000 to 50,000 and having the structure:

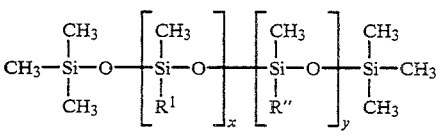

where
the groups R' and R" are each chosen from —H, $C_{1-18}$ alkyl and

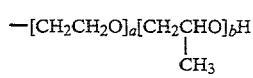

a has a value of from 9 to 115,
b has a value of from 0 to 50,
x has a value of from 133 to 673,
y has a value of from 25 to 0.25.

Preferably, the dimethyl polysiloxane polymer is one in which:
a has a value of from 10 to 114
b has a value of from 0 to 49
x has a value of from 388 to 402
y has a value of from 15 to 0.75
one of groups R' and R" being lauryl, and the other having a molcular weight of from 1000 to 5000.

A particularly preferred dimethyl polysiloxane polymer is one in which:
a has the value 14
b has the value 13
x has the value 249
y has the value 1.25

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

Other Cosmetic Adjuncts

Examples of conventional adjuncts which can optionally be employed include preservatives, such as parahydroxy benzoate esters; antioxidants, such butyl hydroxy toluene; humectants, such as glycerol, sorbitol, 2-pyrrolidone-5-carboxylate, dibutylphthalate, gelatin, polyethylene, glycol, preferably PEG 200-600; buffers, such as lactic acid together with a base such as triethanolamine or sodium hydroxide; surfactants, such as glycerol ethers and other ceramides of synthetic, animal or plant origin; phospholipids; waxes, such as beeswax, ozokerite wax, paraffin wax, plant extracts, such as Aloe vera, cornflower, witch hazel, elderflower, cucumber; thickeners; activity enhancers; colourants; perfumes; and sunscreen materials such as ultrafine titanium dioxide and organic sunscreens such as p-aminobenzoic acid and esters thereof, ethylhexyl p-methoxycinnamate, 2-ethoxyethyl p-methoxycinnamate and butyl methoxydibenzoylmethane, and mixtures thereof.

In a further preferred composition, the modified ceramide, or a mixture thereof is combined with conventional ceramides, pseudoceramides, cholesterol, cholesterol fatty acids, fatty acids, triglycerides, cerebroside, phospholipid and other ingredients well known to those skilled in the art to produce a liposomal dispersion.

In yet another preferred composition, the modified ceramide, or mixture thereof, is dissolved in squalene or squalane, optionally together with conventional ceramides, and formulated with volatile and non-volatile silicones to produce an anhydrous or nearly anhydrous single phase system.

Cosmetic adjuncts can form the balance of the composition.

Use of the Composition

The composition according to the invention is intended primarily as a product for topical application to human skin, especially as an agent for reducing the permeability to water of the skin, particularly when the skin is dry or damaged, in order to reduce moisture loss and generally to enhance the quality of skin. The composition can also be applied to hair and nails.

The modified ceramides according to the invention have surfactant properties and can therefore also be used, in the form of a composition as herein defined, for cleansing the surface of the human body. In particular the composition can be used to cleanse the skin to remove make up or can be employed in a shampoo for cleansing the hair.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

PRODUCT FORM AND PACKAGING

The topical skin, hair or nail treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas, or above. The composition can be packaged in a suitable container to suit its viscosity and intended use by the consumer.

For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

EXAMPLES

The invention is illustrated by the following examples.

Example 1

This example illustrates a high internal phase water-in-oil emulsion in accordance with the invention. A high internal phase water-in-oil emulsion having the following formulation was prepared:

|  | % w/w |
|---|---|
| Fully hydrogenated coconut oil | 3.9 |
| Phosphorylated ceramide having the structure (8) | 0.1 |
| Brij 92* | 5 |
| Bentone 38 | 0.5 |
| Preservative | 0.3 |
| $MgSO_4 7H_2O$ | 0.3 |
| Butylated hydroxy toluene | 0.01 |
| Perfume | qs |
| Water | to 100 |

*Brij 92 is polyoxyethylene (2) oleyl ether

Example 2

This example also illustrates a high internal phase water-in-oil emulsion in accordance with the invention in which the formulation of Example 1 was prepared but with the following changes:
 i. liquid paraffin replaced the fully hydrogenated coconut oil, and
 ii. the modified ceramide was sulphated and had the structure (9).

Example 3

This example also illustrates a high internal phase water-in-oil emulsion in accordance with the invention in which the formulation of Example 1 was prepared but with the following changes:

The phosphorylated ceramide had the structure (10).

Example 4

This example illustrates an oil-in-water cream containing an ester of the invention.

An oil-in-water cream emulsion having the following formulation was prepared:

|  | % w/w |
|---|---|
| Mineral oil | 4 |
| Sulphated ceramide having the structure (11) | 0.1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water | to 100 |

*Brij 56 is cetyl alcohol POE (10)
Alfol 16RD is cetyl alcohol

Example 5

This example also illustrates an oil-in-water emulsion in accordance with the invention, in which the formulation of example 4 was prepared but with the following change:
 the modified ceramide was phosphorylated and had the structure (12), as herein defined.

Example 6

This example also illustrates an oil-in-water emulsion in accordance with the invention, in which the formulation of example 4 was prepared but with the following changes:

sulphated ceramide was that having the structure (13) as herein defined.

Example 7

This example illustrates an alcoholic lotion containing an amide of the invention.

The lotion had the following formulation:

|  | % w/w |
|---|---|
| Phosphorylated ceramide having the structure (14) | 0.2 |
| Ethanol | 40 |
| Perfume | qs |
| Butylated hydroxy toluene | 0.01 |
| Water | to 100 |

Example 8

This example illustrates an alcoholic lotion containing an amide of the invention.

The lotion had the following formulations:

|  | % w/w |
|---|---|
| Sulphated ceramide having the structure (15) | 0.2 |
| Dimethylsulphoxide | 10 |
| Ethanol | 40 |
| Antioxidant | 0.1 |
| Perfume | qs |
| Water | to 100 |

Examples 9 and 10

The following compositions according to the invention represent lotions which can be used in the treatment of dry skin:

|  | % w/w | |
|---|---|---|
|  | 9 | 10 |
| Phosphorylated ceramide having the structure (16) | 1.5 | — |
| Sulphated ceramide having the structure (17) | — | 0.5 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilised demineralised water | to 100 | to 100 |

Examples 11 and 12

The following compositions according to the invention represent lotions which can be used in the treatment of dry skin:

|  | % w/w | |
|---|---|---|
|  | 11 | 12 |
| The phosphorylated ceramide having the structure (18) | 0.08 | — |
| The sulphated ceramide having the structure (19) | — | 0.15 |
| Ethanol | 10 | 10 |
| Perfume | 0.5 | 0.5 |
| Distilled water | to 100 | to 100 |

Example 13

This example illustrates a high internal phase water-in-oil emulsion in accordance with the invention.

A high internal phase water-in-oil emulsion having the following formulation was prepared:

|  | % w/w |
|---|---|
| Fully hydrogenated coconut oil | 3.9 |
| Phosphorylated ceramide having the structure (20) | 0.1 |
| Brij 92* | 5 |
| Bentone 38 | 0.5 |
| Preservative | 0.3 |
| $MgSO_4 7H_2O$ | 0.3 |
| Butylated hydroxy toluene | 0.01 |
| Perfume | qs |
| Water | to 100 |

*Brij 92 is polyoxyethylene (2) oleyl ether

Example 14

This example also illustrates a high internal phase water-in-oil emulsion in accordance with the invention in which the formulation of Example 1 was prepared but with the following changes:

i. liquid paraffin replaced the fully hydrogenated coconut oil, and ii. the phosphorylated ceramide had the structure (21).

Example 15

This example also illustrates a high internal phase water-in-oil emulsion in accordance with the invention in which the formulation of Example 1 was prepared but with the following changes:

The phosphorylated ceramide had the structure (22).

Example 16

This example illustrates an oil-in-water cream containing an ester of the invention.

An oil-in-water cream emulsion having the following formulation was prepared:

|  | % w/w |
|---|---|
| Mineral oil | 4 |
| Sulphated ceramide having the structure (23) | 0.1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water | to 100 |

*Brij 56 is cetyl alcohol POE (10)
Alfol 16RD is cetyl alcohol

Example 17

This example also illustrates an oil-in-water emulsion containing an ester of the invention, in which the formulation of example 4 was prepared but with the following change:

the sulphated ceramide was that having structure (24), as herein defined.

Example 18

This example also illustrates an oil-in-water emulsion in accordance with the invention, in which the formulation of example 4 was prepared but with the following changes:

the modified ceramide was both sulphated and phosphorylated and had the structure (25) as herein defined.

Example 19

This example illustrates an alcoholic lotion containing an amide of the invention.

The lotion had the following formulation:

|  | % w/w |
|---|---|
| Phosphorylated ceramide having the structure (8) | 0.2 |
| Ethanol | 40 |
| Perfume | qs |
| Butylated hydroxy toluene | 0.01 |
| Water | to 100 |

Example 20

This example illustrates an alcoholic lotion containing an amide of the invention which is suitable for application to nails, The lotion had the following formulations:

|  | % w/w |
|---|---|
| Sulphated ceramide having the structure (9) | 0.2 |
| Dimethylsulphoxide | 10 |
| Ethanol | 40 |
| Antioxidant | 0.1 |
| Perfume | qs |
| Water | to 100 |

Examples 21 and 22

The following compositions according to the invention represent lotions which can be used in the treatment of dry, unmanageable hair.

|  | % w/w | |
|---|---|---|
|  | 21 | 22 |
| Phosphorylated ceramide having the structure (10) | 1.5 | — |
| Sulphated ceramide having the structure (11) | — | 0.5 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilised demineralised water | to 100 | to 100 |

Examples 23 and 24

The following compositions according to the invention represent lotions which can be used in the treatment of dry skin, hair or nails:

|  | % w/w | |
|---|---|---|
|  | 23 | 24 |
| The phosphorylated ceramide having the structure (12) | 0.08 | — |
| The sulphated ceramide having the structure (13) | — | 0.15 |
| Ethanol | 10 | 10 |
| Perfume | 0.5 | 0.5 |
| Distilled water | to 100 | to 100 |

Example 25

This example also illustrates an oil-in-water emulsion in accordance with the invention, in which the formulation of example 4 was prepared but with the following change:

the modified ceramide was phosphorylated and had the structure (12), as herein defined.

We claim:

1. A composition suitable for topical application to skin, hair or nails, which comprises an amount of from 0.00001 to 20% by weight of a modified ceramide, together with a cosmetically acceptable vehicle for the modified ceramide, the modified ceramide having the structure (1):

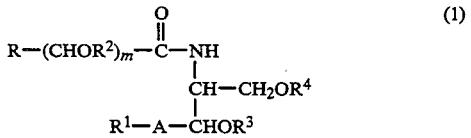

where A represents $-CH_2$ or $-CHOR^2$ or $-CH=CH-$ or $-CHOY$;

R represents a linear or branched, saturated or unsaturated aliphatic hydrocarbon group having from 8 to 49 carbon atoms which may be substituted with a hydroxyl group, phosphate group or sulphate group or the group $Y-O-(C_aH_b)-$ $R^1$ represents a linear or branched, saturated or unsaturated aliphatic hydrocarbon having from 8 to 28 carbon atoms which may be substituted with a hydroxyl group, a phosphate group or a sulphate group;

$R^2$ & $R^3$ individually represent a phosphite group ($P_i$), or a-sulphite group ($SO_3^{\ominus}$), $P_i$ represents:

$R^4$ represents H, a phosphite group ($P_i$), a sulphite group $SO_3^-$, a glucosyl group or the groups

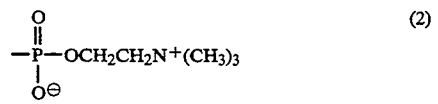

-continued

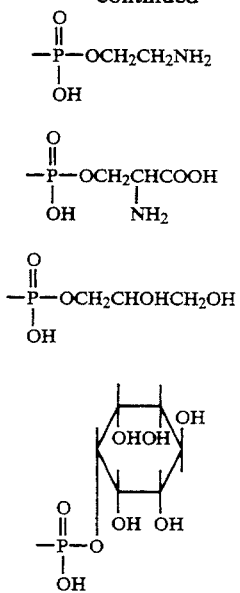

a is an integer of from 7 to 49
b is an integer of from 10 to 98
m is 0 or 1
Y represents H or a residue of a $C_{14}$ to $C_{22}$ fatty acid having the structure (7)

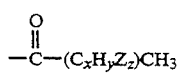

where
z is —OH or an epoxy oxygen
x is an integer of from 12 to 20
y is an integer of from 20 to 40
z is 0, or an integer of from 1 to 4.

2. A composition according to claim 1 wherein $R^4$ is not H.

3. A method for the treatment of skin, hair or nails which comprises topical application an effective amount of a composition according to claim 1.

4. A method of repairing skin water barrier, the method comprising applying to skin a topical composition according to claim 1.

5. A method of treating nails, the method comprising applying to nails a composition according to claim 1.

6. A method of treating hair, the method comprising applying to hair a composition according to claim 1.

7. Modified ceramides having the structure:

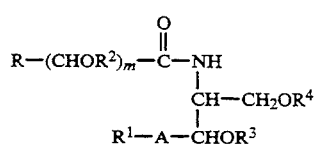

where A represents —$CH_2$ or —$CHOR^2$ or —CH=CH— or —CHOY;

R represents a linear or branched, saturated or unsaturated aliphatic hydrocarbon group having from 8 to 49 carbon atoms which may be substituted with a hydroxyl group, phosphate group or sulphate group or the group Y—O—($C_aH_b$)—

$R^1$ represents a linear or branched, saturated or unsaturated aliphatic hydrocarbon having from 8 to 28 carbon atoms which may be substituted with a hydroxyl group, a phosphate group or a sulphate group;

$R^2$ & $R^3$ individually represent a phosphite group ($P_i$), or a sulphite group ($SO_3^\ominus$), $P_i$ represents:

$R^4$ represents H, a phosphite group ($P_i$), a sulphite group $SO_3^-$, a glucosyl group or the groups

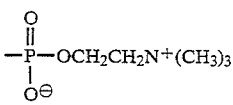

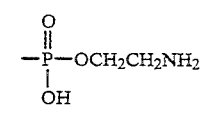

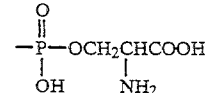

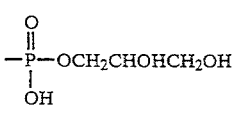

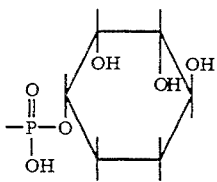

a is an integer of from 7 to 49
b is an integer of from 10 to 98
m is 0 or 1
Y represents H or a residue of a $C_{14}$ to $C_{22}$ fatty acid having the structure (7)

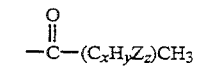

where
z is —OH or an epoxy oxygen
x is an integer of from 12 to 20
y is an integer of from 20 to 40
z is 0, or an integer of from 1 to 4.

* * * * *